United States Patent
Qian et al.

(10) Patent No.: US 8,557,147 B2
(45) Date of Patent: Oct. 15, 2013

(54) CHEMILUMINESCENT COMPOSITIONS, ENHANCING REAGENTS FOR CHEMILUMINESCENCE AND METHODS FOR THE PREPARATION AND USE THEREOF

(75) Inventors: Chungen Qian, Shenzen (CN); Yuping Zhang, Shenzen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 63 days.

(21) Appl. No.: 13/172,306

(22) Filed: Jun. 29, 2011

(65) Prior Publication Data

US 2012/0001136 A1    Jan. 5, 2012

(30) Foreign Application Priority Data

Jun. 30, 2010    (CN) .......................... 2010 1 0215774

(51) Int. Cl.
*C09K 11/07*    (2006.01)
*C07C 211/27*    (2006.01)

(52) U.S. Cl.
USPC ......................................... 252/700; 564/384

(58) Field of Classification Search
USPC ......................................... 252/700; 564/384
See application file for complete search history.

(56) References Cited

U.S. PATENT DOCUMENTS

| | | | |
|---|---|---|---|
| 4,857,652 A | 8/1989 | Schaap | |
| 4,959,182 A | 9/1990 | Schaap | |
| 5,004,565 A | 4/1991 | Schaap | |
| 5,145,772 A | 9/1992 | Voyta et al. | |
| 5,393,469 A | 2/1995 | Akhavan-Tafti | |
| 5,547,836 A | 8/1996 | Bronstein et al. | |
| 5,650,099 A | 7/1997 | Akhavan-Tafti et al. | |
| 7,091,051 B2 * | 8/2006 | Kitaoka et al. | 436/546 |
| 2002/0019553 A1 | 2/2002 | Akhavan-Tafti et al. | |
| 2009/0081696 A1 | 3/2009 | Sugiyama | |

FOREIGN PATENT DOCUMENTS

CN    1719254    1/2006

OTHER PUBLICATIONS

Schaap et al. Clinical Chemistry, vol. 35, No. 9, 1989, pp. 1863-1864.
Sha et al., 'Progress of Research on Chemiluminescene Enzyme Immunoassay', College of Chemistry, Beijing Normal University, Beijing 100875 China, PTCA (Part B: Chem. Anal.) 2010.

(Continued)

*Primary Examiner* — Vu A Nguyen
(74) *Attorney, Agent, or Firm* — Stoel Rives LLP; Kory D. Christensen; Matthew S. Bethards

(57) ABSTRACT

The present disclosure provides a chemiluminescent composition where the chemiluminescent substrate is 1,2-dioxetane, which contains 1,2-dioxetane and an alkyl dimethyl benzyl quaternary ammonium salt having the structure of general formula I. The present disclosure also provides an enhancing reagent and methods for enhancing chemiluminescence of 1,2-dioxetane, where the enhancing reagent contains an alkyl dimethyl benzyl quaternary ammonium salt having the structure of general formula I.

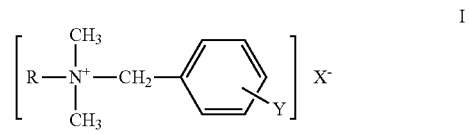

17 Claims, 2 Drawing Sheets

(56) References Cited

OTHER PUBLICATIONS

Waschinski et al., 'Design of Contact—Active Antimocribial Acrylate-Based Materials Using Biocidal Macromers.' Advanced Materials, Wiley Interscience, Advanced Materials 2008, 20, pp. 104-108.

U.S. Appl. No. 13/172,140, filed Jun. 29, 2011, Qian.

U.S. Appl. No. 13/177,189, filed Jul. 6, 2011, Qian.

Office Action dated Nov. 6, 2012 for U.S. Appl. No. 13/172,140.

Restriction Requirement dated Aug. 13, 2012 for U.S. Appl. No. 13/172,140.

Restriction Requirement dated Apr. 4, 2013 for U.S. Appl. No. 13/177,189.

Office Action dated May 16, 2013 for U.S. Appl. No. 13/177,189.

* cited by examiner

CHEMILUMINESCENT COMPOSITIONS, ENHANCING REAGENTS FOR CHEMILUMINESCENCE AND METHODS FOR THE PREPARATION AND USE THEREOF

RELATED APPLICATIONS

This application claims priority to Chinese Patent Application No. 201010215774.8, filed Jun. 30, 2010, for "CHEMILUMINESCENT COMPOSITION, ENHANCING REAGENT FOR CHEMILUMINESCENCE AND METHOD THEREOF," the disclosure of which is fully incorporated herein by reference.

FIELD OF DISCLOSURE

The present disclosure relates to the field of chemiluminescence immunoassays, particularly reagents and methods for enhancing the chemiluminescence of a 1,2-dioxetane compound, preparation methods and kits thereof, chemiluminescent compositions containing the enhancing reagents, preparation methods and kits thereof.

DETAILED DESCRIPTION OF THE DISCLOSURE

Figure 1:
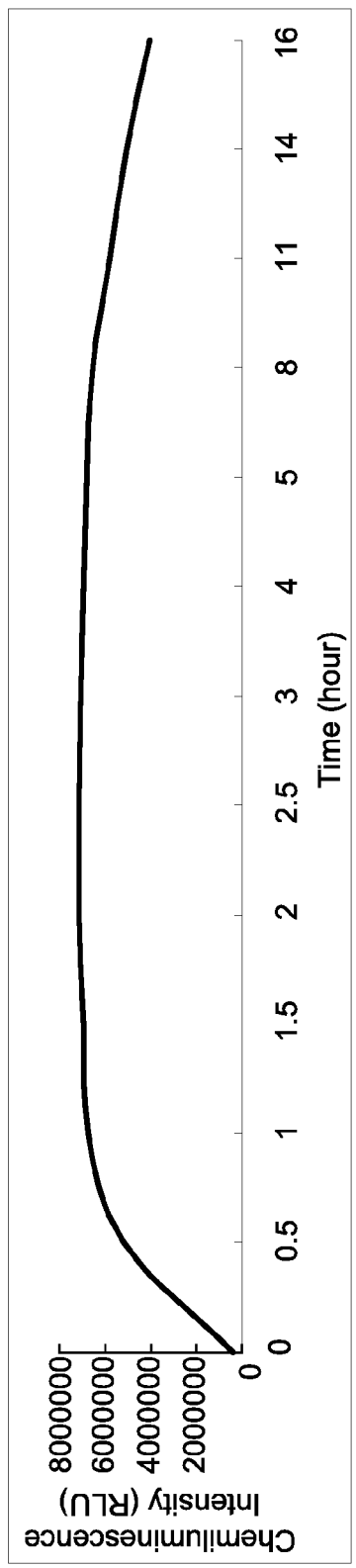
FIG. 1 shows a plot of relative luminescence intensity vs. time for the chemiluminescent composition according to Example 18, wherein the X-axis is time and the Y-axis is luminescence intensity.

As a non-radioactive immunoassay technology, chemiluminescence immunoassays developed very quickly in the world after enzyme immunoassay (EIA), radioimmunoassay, and fluorescence immunoassay technologies. Chemiluminescence immunoassay is a microassay technology which has high sensitivity, wide detection range, simple and fast operation, stable label, and low contamination, making it a desirable quantitative immunoassay method.

Luminol, isoluminol, acridine esters, and 1,2-dioxetane compounds are used as luminescent substances in chemiluminescence immunoassays. Isoluminol and acridine esters are labeled directly and act as tracing molecules in flash-type chemiluminescent reactions. However, Luminol and the 1,2-dioxetane compounds are activated by enzymes and act as tracing molecules after enzymatic catalysis in a glow-type chemiluminescent reaction. The 1,2-dioxetane compounds are alkaline phosphatase (ALP) substrates with ultra-high sensitivity. When they contact ALP in appropriate buffers, ALP will hydrolyze them to provide strong optical signals which can be maintained over 20 hours. So, 1,2-dioxetane compounds are regarded as desirable chemiluminescent substances. Several manufacturers have developed kits where ALP is the labeling enzyme and 1,2-dioxetane compounds are ALP's substrates. These kits were used in some automatic chemiluminescence systems, for example, developed by DPC, Beckman, BioMerieux, and Olympus.

Some 1,2-dioxetane compounds such as CSPD, CDP, CDP-Star, and BZPD and luminescent compositions thereof are patented and have good luminescence and high prices. Another 1,2-dioxetane compound, 3-(2-spiroadamantane)-4-methoxy-4-(3-phosphoryloxy)phenyl-1,2-dioxetane (AMPPD), is widely known but the optical signal intensity is much weaker than that of the compounds above.

The molecular structure of AMPPD has a four-member heterocycle with a very weak —O—O— bond and a phosphate group, in which the phosphate group maintains the stability of the whole molecular structure. Normally, this compound is very stable, and is scarcely decomposed when stored at 5° C. as a solid. After catalysis by alkaline phosphatase, AMPPD is hydrolyzed at the phosphate group to form a labile intermediate. The intermediate automatically decomposes, with the four-member heterocycle with an —O—O— bond releasing a great deal of energy, thus exciting a chemiluminescent reaction, and emitting photons.

In 1989, Schaap reported a technology for enhancing the chemiluminescence of 1,2-dioxetane compounds using cetyltrimethylammonium bromide and 5-(N-tetradecanoyl)-aminofluoroescein (Clin. Chem., 35). In U.S. Pat. No. 4,959,182 and U.S. Pat. No. 5,004,565, and Chinese Patent CN89106249.1, Schaap describes methods for enhancing chemical and enzymatic triggered chemiluminescence of 1,2-dioxetane compounds by forming a micelle using cetyltrimethylammonium bromide.

U.S. Pat. No. 5,145,772 discloses that poly(vinylbenzyldimethylbenzylammonium chloride) (BDMQ) and a macromolecular substance such as serum albumin can enhance luminescence of 1,2-dioxetane compounds. U.S. Pat. No. 5,547,836 discloses that poly(vinylbenzyltrimethylammonium chloride) (TMQ) and poly(vinylbenzyltributylammonium chloride) (TBQ) are useful as enhancing reagents for luminescence of the 1,2-dioxetane compounds.

U.S. Pat. No. 5,393,469 discloses that polymeric quaternary phosphonium salt provides enhanced chemiluminescence from enzymatically triggered 1,2-dioxetane compounds.

U.S. Pat. No. 5,650,099 and Chinese Patent CN1208399A disclose that dual-cationic surfactants such as trioctylphosphinemethyl-4-tributylphosphinemethylphenyl dichloride, and fluorescent substances such as fluoroescein and hydroxypyrenesulfonic acid, provide enhanced luminescence from 1,2-dioxetane compounds.

Chinese Patent CN1719254A discloses a chemiluminescent composition including CSPD as substrate and enhancing reagents containing cetyltrimethylammonium chloride, myristoylglycerol phosphate disodium, bovine serum albumin, and octadecylamino fluoroescein.

Most of the enhancing reagents for enhancing luminescence of the 1,2-dioxetane compounds disclosed in the patents above are polymers and long-chain alkyl fluorescent substances, and they are expensive and not easily available.

Therefore, this disclosure provides a new chemiluminescent composition, a new reagent and a method for enhancing the luminescence of 1,2-dioxetane compounds.

The present disclosure relates to chemiluminescent compositions containing 1,2-dioxetane compounds and at least one alkyl dimethyl benzyl quaternary ammonium salt having the structure of General Formula I:

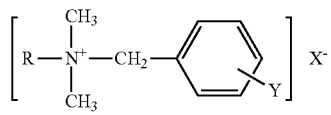

wherein, R is selected from $C_{8-20}$ alkyl or $C_{8-20}$ alkenyl, for example R may be $C_{12-18}$ alkyl; $X^-$ is a negative ion; and Y is a benzene ring substituent, each of which is independently selected from hydrogen, halogen, hydroxyl, sulfhydryl, cyano, nitro, alkyl, alkoxy, haloalkyl, amino, alkylamino, and amido.

In a second aspect, the present disclosure relates to methods for preparing chemiluminescent compositions and chemiluminescent kits including the chemiluminescent compositions.

In a third aspect, the present disclosure relates to enhancing reagents for chemiluminescence of 1,2-dioxetanes, which include at least one alkyl dimethyl benzyl quaternary ammonium salt having the structure of General Formula I, wherein, R is selected from $C_{8-20}$ alkyl or $C_{8-20}$ alkenyl, for example R may be $C_{12-18}$ alkyl; $X^-$ is a negative ion; and Y is a benzene ring substituent, each of which is individually selected from: hydrogen, halogen, hydroxyl, sulfhydryl, cyano, nitro, alkyl, alkoxy, haloalkyl, amino, alkylamino, and amido.

In a fourth aspect, the present disclosure relates to enhancing reagent kits for chemiluminescence of 1,2-dioxetanes. The kits include the enhancing reagents and other components optionally stored individually or in the form of one or more mixtures.

In a fifth aspect, the present disclosure relates to methods for enhancing chemiluminescence of 1,2-dioxetanes, the methods comprising adding at least one alkyl dimethyl benzyl quaternary ammonium salt having the structure of General Formula I into a 1,2-dioxetane solution, wherein, R is selected from $C_{8-20}$ alkyl or $C_{8-20}$ alkenyl, for example R may be $C_{12-18}$ alkyl; Y is a benzene ring substituent, each of which is independently selected from hydrogen, halogen, hydroxyl, sulfhydryl, cyano, nitro, alkyl, alkoxy, haloalkyl, amino, alkylamino, and amido; and $X^-$ is a negative ion.

In a sixth aspect, the present disclosure relates to the use of an alkyl dimethyl benzyl quaternary ammonium salt having the structure of General Formula I in preparation of chemiluminescent compositions.

Chemiluminescent enhancing reagents of the present disclosure have simple components and desirable enhancing effects for 1,2-dioxetanes. The chemiluminescent compositions of the present disclosure provide stable, long-lasting and greatly enhanced chemiluminescence signals and may be used in chemiluminescence immunoassays, DNA probe detection, and chemiluminescence analysis of biological membrane protein blotting. The chemiluminescent compositions of the present disclosure may be widely used in the fields of clinical diagnosis, scientific research, environmental and hygiene detection, and forensic identification.

In order to make other aspects and advantages of the present disclosure more apparent, the present disclosure is illustrated with reference to the following description and specific embodiments.

DEFINITIONS

Unless indicated otherwise, terms used herein have the following meanings.

The term "alkyl" as used herein individually or in combination with other groups refers to straight or branched alkyl groups containing 1-18 carbon atoms, such as 1-12, 1-8, and 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

The term "aryl" as used herein refers to an optionally substituted aromatic carbocyclic group, such as monocylic or bicylic groups having 6-12 carbon atoms in the ring moiety, for example, phenyl, biphenyl, naphthyl, substituted phenyl; substituted biphenyl, or substituted naphthyl. Examples of aryl groups are phenyl or substituted phenyl.

The term "halogen" as used herein includes fluorine, chlorine, bromine, and iodine.

The term "alkyloxy" as used herein refers to "alkyl" as defined above attached to the group —O—, wherein said "alkyl" contains 1-18 carbon atoms, for example 1-12, or alternatively 1-8, or 1-6 carbon atoms, such as methoxy, ethoxy and propoxy.

Unless otherwise indicated, the term "a soluble salt" as used herein refers to a water soluble salt, and includes, but is not limited to, halide, sulfate, carbonate, and phosphate.

Chemiluminescent Compositions

Chemiluminescence is light generated in a specific reaction of a chemical substance. Singlet molecules are excited and formed as high energy intermediates decompose in a chemical reaction, then the excited singlet molecules return to the ground state, and part of the energy is emitted in the form of luminescence. Therefore, chemiluminescent reactions include two processes: an excitation process and a luminescence process. Some molecular energy will also be dissipated in the excited state because of inter- and intra-system crossing.

The 1,2-dioxetane compounds are chemiluminescent substrates, and their structures are well-known in the art. A typical structure is as follows:

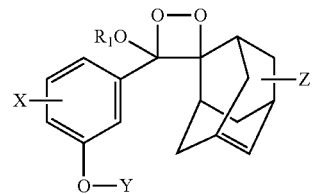

wherein $R_1$ is selected from at least one of the following: alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, and halogenated alkyl acid; X is hydrogen or a substituent on a phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on an adamantane ring.

The 1,2-dioxetane compounds used herein include, but are not limited to, 3-(2'-spiroadamantane)-4-methoxy-4-(3"-phosphoryloxy)phenyl-1,2-dioxetane (AMPPD), disodium 3-(4-methoxyspiro{1,2-dioxetane-3,2'-(5'-chloro)tricyclo

[3.3.1.1³,⁷]decan}-4-yl)phenyl phosphate (CSPD), and disodium 2-chloro-5-(4-methoxyspiro{1,2-dioxetane-3,2'-(5'-chloro)-tricyclo[3.3.1.1³,⁷]decan}-4-yl)-1-phenyl phosphate (CDP-Star).

AMPPD can be effectively decomposed by an alkaline phosphatase, by removal of a phosphate group to form an AMPPD intermediate. The intermediate is cleaved into adamantanone and a meta-oxy methyl benzoate anion in the excited state through inter-molecular electron transfer. When the meta-oxy methyl benzoate anion transitions from the excited state to the ground state, light with a maximal wavelength of 477 nm is generated. Chemiluminescence from AMPPD catalyzed with an alkaline phosphatase can reach its peak at 15 min of reaction time, and then the optical signal strength remains relatively constant for between 15 to 60 min, with small variation. Chemiluminescence measurements may still be correct even after 12 h. AMPPD is used in a range of 0.0001-0.01 mol/L.

A person of skill in the art can understand that, based on different cleavable groups, 1,2-dioxetane compounds can be activated using different enzymes, for example, galactosidase, glucose oxidase, and catalase. In addition, Y may be chemically cleaved, to activate the 1,2-dioxetane compounds to emit light.

In chemiluminescence immunoassays, it is expected that chemical bond energy is converted into light energy as efficiently as possible, and that the generated chemiluminescence signal intensity is high and stable. The efficiency of the chemiluminescent reaction is dependent on the quantum efficiency of generating fluorescence and phosphorescence. Methods for improving the chemiluminescence intensity include: improving the quantum yield of luminescent substrate molecules, improving the enzyme activity, and stabilizing the luminescent molecules in the excited state.

In one aspect, the present disclosure provides chemiluminescent compositions, which include 1,2-dioxetane compounds and at least one alkyl dimethyl benzyl quaternary ammonium salt having a structure of General Formula I

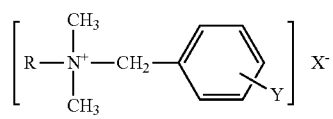

I wherein, R is selected from $C_{8-20}$ alkyl or $C_{8-20}$ alkenyl, for example R may be $C_{12-18}$ alkyl; $X^-$ is a negative ion; Y is a benzene ring substituent, each of which is independently selected from: hydrogen, halogen, hydroxyl, sulfhydryl, cyano, nitro, alkyl, alkoxy, haloalkyl, amino, alkylamino, and amido.

The alkyl dimethyl benzyl quaternary ammonium salts used herein are a kind of cationic surfactant, which are stable and easily dissolved in water. In some embodiments, the alkyl dimethyl benzyl quaternary ammonium salt is selected from at least one of the following: a hexadecyl dimethyl benzyl ammonium salt, an octadecyl dimethyl benzyl ammonium salt, a dodecyl dimethyl benzyl ammonium salt, a myristyl dimethyl benzyl ammonium salt and combinations thereof. In other embodiments, the alkyl dimethyl benzyl quaternary ammonium salts include, but are not limited to hexadecyl dimethyl benzyl ammonium chloride (1813 surfactant), octadecyl dimethyl benzyl ammonium chloride (1827 surfactant), dodecyl dimethyl benzyl ammonium chloride, myristyl dimethyl benzyl ammonium chloride, dodecyl dimethyl benzyl ammonium bromide, myristyl dimethyl benzyl ammonium bromide, hexadecyl dimethyl benzyl ammonium bromide, octadecyl dimethyl benzyl ammonium bromide. They are mainly used as cosmetic antiseptic cleaners, hair conditioners, softeners and emulsifiers.

While not being bound by theory, it is believed that the surfactants used in the embodiments of the present disclosure may form micelles in a solution, whose micro environment is non-aqueous. In the non-aqueous environment, the chemiluminescent reaction efficiency and quantum yield improve. Meanwhile, the surfactants may be conducive to the fluorescent molecules moving close to the chemiluminescent substrate molecules, allowing light energy transfer to occur once the chemiluminescence reaction starts. The quantum yield of the fluorescent molecules is much greater than that of the chemiluminescent molecules, thus enhancing the optical signal. The alkyl dimethyl benzyl quaternary ammonium salt is generally used at a concentration of 0.1 g/L to 10 g/L, for example 1 g/L to 10 g/L.

The chemiluminescent compositions according to the embodiments of the present disclosure may further include fluorescent agents, for example, fluorescein sodium, Rhodamine B, and Rhodamine 6G. The fluorescent agents will emit another kind of fluorescence after receiving light energy from the luminescent substance. The quantum yield of fluorescein is far greater than that of the chemiluminescent substance, so the quantum yield of the luminescent substance may indirectly improve. For example, fluorescein sodium (9-(o-carboxyphenyl)-6-hydroxy-3H-xanthene-3-ketone disodium) is a water soluble fluorescent agent, and has an excitation and emission wavelength of 494 nm and 518 nm respectively. The quantum yield of fluorescein sodium is up to 0.97. Similarly, Rhodamine series fluorescent agents also have a very high fluorescence quantum yield. The fluorescent agent is used at concentration of about 0.1 mg/L to about 1 g/L.

The chemiluminescent compositions of the present disclosure may further contain a buffer, for maintaining the pH of the reaction system. Appropriate buffers include a carbonate buffer, a diethanolamine buffer, 2-amino-2-methyl-1-propanol, and so on. When luminescence of a chemiluminescent substance is triggered by cleavage of the phosphate group, an appropriate buffer may be a 2-amino-2-methyl-1-propanol buffer system. For example, in a reaction process where phosphate groups are cleaved by catalysis of alkaline phosphatase, 2-amino-2-methyl-1-propanol may be a phosphate receptor in phosphotransfer, so as to improve the catalytic effect of ALP. As for the alkaline phosphatase system, the most suitable pH for reaction may range from about 9 to about 10. The buffer may be used at an concentration of about 10 to about 500 mM.

The chemiluminescent compositions of the present disclosure may further contain magnesium ions, which are from soluble salts containing magnesium ions, for example, magnesium sulfate, magnesium acetate, magnesium chloride, and other salts from which magnesium ions can be dissociated in solution. When a 1,2-dioxetane compound containing a phosphate group is used as a chemiluminescent substrate, the phosphate group can be hydrolyzed by alkaline phosphatase, thus producing chemiluminescence. In this case, the addition of magnesium ions can activate alkaline phosphatase, thereby improving the catalytic performance of alkaline phosphatase for the hydrolysis reaction. The magnesium ions are used at a concentration range from about 0.001 to about 0.01 mol/L.

The chemiluminescent compositions of the present disclosure may further include a preservative, which facilitates the preservation and long-term storage of the reagent. There is no limitation to the type of the preservative, and commercially available preservatives such as Proclin300, sodium azide, Kathon, and Gentamicin may be used. The preservatives may be used at any concentration which will not influence the chemiluminescent reaction and the activity of alkaline phosphatase.

To prepare the chemiluminescent compositions according to the embodiments of the present disclosure, the components in the chemiluminescent compositions above are dissolved in pure water, optionally adjusted to a desired pH and brought up to the final volume with water. The pH may be adjusted according to the conditions required for activating the substrate. For example, if the substrate is activated by an alkaline phosphatase, the pH of chemiluminescent compositions may be adjusted to the range of about 9 to about 10.

The chemiluminescent composition according to the embodiments of the present disclosure may be made into a kit by individually packaging the components of the chemiluminescent composition into a multi-package system. In other embodiments, some components may be combined in one container, while the others are stored in separate containers to form a multi-package system. Alternatively, the components may be mixed, and then packaged as a single mixture. According to different detection uses, the kit may further include corresponding enzyme reagents, labeled enzyme reagent, a solid-phase antibody or a manual which instructs the operator.

Enhancing Reagents for Enhancing Chemiluminescence

In one aspect, the present disclosure provides enhancing reagents for chemiluminescence of 1,2-dioxetanes, in which the enhancing reagents contain at least one alkyl dimethyl benzyl quaternary ammonium salt having a structure of general formula I

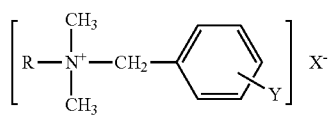

wherein, R is selected from $C_{8-20}$ alkyl or $C_{8-20}$ alkenyl, for example R may be $C_{12-18}$ alkyl; $X^-$ is a negative ion; Y is a benzene ring substituent, each of which is independently selected from: hydrogen, halogen, hydroxyl, sulfhydryl, cyano, nitro, alkyl, alkoxy, haloalkyl, amino, alkylamino, and amido.

The alkyl dimethyl benzyl quaternary ammonium salts used herein are a kind of cationic surfactant. They include, but are not limited to hexadecyl dimethyl benzyl ammonium chloride (1813 surfactant), octadecyl dimethyl benzyl ammonium chloride (1827 surfactant), dodecyl dimethyl benzyl ammonium chloride, myristyl dimethyl benzyl ammonium chloride, dodecyl dimethyl benzyl ammonium bromide, myristyl dimethyl benzyl ammonium bromide, hexadecyl dimethyl benzyl ammonium bromide, octadecyl dimethyl benzyl ammonium bromide. They are generally used at an concentration of 0.1 g/L to 10 g/L.

The enhancing reagents of the present disclosure may further include optional fluorescent agents, optional magnesium ions, optional buffers, and optional preservatives, which have the same definitions as the corresponding components in the chemiluminescent compositions above. The buffer may be a 2-amino-2-methyl-1-propanol buffer system.

To prepare the enhancing reagents, components of the enhancing reagent are dissolved in pure water, the pH is optionally adjusted, and water is added to final volume.

The enhancing reagents of the present disclosure also may be made into a kit for commercial use by individually packaging the components of the enhancing reagent into a multi-package system. In other embodiments, some components may be combined in one container, while the others are stored in separate containers to form a multi-package system. Alternatively, the components may be mixed, and then packaged as a single mixture. The kit may further include manuals which instruct the operator.

Method for Enhancing Chemiluminescence

The present disclosure further provides a method for enhancing luminescence of 1,2-dioxetane compounds, which includes adding the chemiluminescent enhancing reagents or one or more components of kits of the present disclosure to a solution containing 1,2-dioxetane compounds.

Use of Alkyl Dimethyl Benzyl Quaternary Ammonium Salt Having a Structure of Formula I in Preparation of Chemiluminescent Compositions The present disclosure provides the use of an alkyl dimethyl benzyl quaternary ammonium salt having the structure of General Formula I in preparation of chemiluminescent compositions. The alkyl dimethyl benzyl quaternary ammonium salts of the present disclosure enhance the chemiluminescence of substances such as 1,2-dioxetane compounds. Moreover, most of these salts are commercially available, inexpensive, and suitable for production of chemiluminescent compositions on a large scale.

EXAMPLES

The present disclosure will be further described with references to the following particular examples. These examples are intended only to be illustrative, but not to limit the scope of the present disclosure in any sense.

Unless otherwise indicated, all of chemical reagents used in the examples were analytic pure, and supplied from Sigma-Aldrich Company. The chemiluminescence analyzer is a BHP9507 chemiluminescence analyzer supplied from Beijing Hamamatsu Photon Techniques Inc.

Examples 1 to 17

A basic luminescent composition was formulated with ultra-pure water as follows:

| | |
|---|---|
| 2-amino-2-methyl-1-propanol | 200 mM |
| AMPPD | 0.5 mM |
| $MgCl_2$ | 5 mM |
| Proclin 300 | 0.5 g/L |
| pH was adjusted with HCl | to 9.5 |

Appropriate amounts of components other than AMPPD were weighed, dissolved into ultra-pure water, pH adjusted, and adjusted to final volume with water. AMPPD was then added and dissolved, to obtain the basic luminescent composition in which the final concentrations of the components were as shown in the table above. Components of the respective enhancing reagent were added to the basic luminescent composition to formulate the chemiluminescent compositions of Example 1-17 (see Table 1).

100 μl of the chemiluminescent composition from each example was added to 50 μl of a 1 ng/mL solution of alkaline phosphatase. Chemiluminescence intensity (RLU) was measured by a chemiluminescence analyzer and the fold increase in RLU was calculated for each chemiluminescent composition versus the basic luminescent composition. As shown in examples 2 to 7 of Table 1, the alkyl dimethyl benzyl quaternary ammonium salt used alone enhances chemiluminescence from the chemiluminescent composition; the effect was similar to that of the fluorescent agent used alone. Examples 8 to 17 of Table 1 also show that the alkyl dimethyl benzyl quaternary ammonium salt and the fluorescent agent act synergistically, significantly enhancing the luminescence signal of AMPPD.

TABLE 1

Chemiluminescent compositions of Examples 1-17 and intensity duration of chemiluminescence from AMPPD

| Example | Enhancing component(s) added to basic luminescent composition | Luminescence intensity (RLU) | Fold Increase in RLU |
|---|---|---|---|
| 1 | No | 7070 | 1.00 |
| 2 | 5 mg/L fluorescein Sodium | 53237 | 7.53 |
| 3 | 1 mg/L Rhodamine 6G | 36411 | 5.15 |
| 4 | 0.1 g/L hexadecyl dimethyl benzyl ammonium chloride | 25099 | 3.55 |
| 5 | 1 g/L hexadecyl dimethyl benzyl ammonium chloride | 28351 | 4.01 |
| 6 | 10 g/L hexadecyl dimethyl benzyl ammonium chloride | 14918 | 2.11 |
| 7 | 1 g/L myristyl dimethyl benzyl ammonium chloride | 34643 | 4.90 |
| 8 | 5 g/L myristyl dimethyl benzyl ammonium chloride, 5 mg/L fluorescein sodium | 769852 | 108.89 |
| 9 | 0.1 g/L hexadecyl dimethyl benzyl ammonium chloride, 5 mg/L fluorescein sodium | 142602 | 20.17 |
| 10 | 5 g/L hexadecyl dimethyl benzyl ammonium chloride, 5 mg/L fluorescein sodium | 999981 | 141.44 |
| 11 | 10 g/L hexadecyl dimethyl benzyl ammonium chloride, 5 mg/L fluorescein sodium | 708768 | 100.25 |
| 12 | 0.1 g/L hexadecyl dimethyl benzyl ammonium chloride, 5 mg/L Rhodamine 6G | 51258 | 7.25 |
| 13 | 10 g/L hexadecyl dimethyl benzyl ammonium chloride, 5 mg/L Rhodamine 6G | 287254 | 40.63 |
| 14 | 5 g/L dodecyl dimethyl benzyl ammonium bromide, 5 mg/L Rhodamine 6G | 228008 | 32.25 |
| 15 | 5 g/L myristyl dimethyl benzyl ammonium bromide, 5 mg/L Rhodamine 6G | 65256 | 9.23 |
| 16 | 5 g/L hexadecyl dimethyl benzyl ammonium bromide, 5 mg/L Rhodamine 6G | 378811 | 53.58 |
| 17 | 5 g/L octadecyl dimethyl benzyl ammonium bromide, 5 mg/L Rhodamine 6G | 276578 | 39.12 |

Example 18

Referring to the method of Example 1, a chemiluminescent composition was prepared as follows:

| | |
|---|---|
| 2-amino-2-methyl-1-propanol | 200 mM |
| AMPPD | 0.5 mM |
| $MgCl_2$ | 5 mM |
| hexadecyl dimethyl benzyl ammonium chloride | 5 g/L |
| Fluorescein Sodium | 5 mg/L |
| Proclin 300 | 0.5 g/L |
| pH was adjusted with HCl | to 9.5 |

100 µl of the chemiluminescent composition was added to 50 µl of a 1 ng/mL solution of alkaline phosphatase. Chemiluminescence intensity was measured by a chemiluminescence analyzer, and a chemiluminescent intensity-time curve was plotted. The results are shown in FIG. 1, which demonstrates that the luminescence signal of the chemiluminescent composition of the present disclosure is stable and long lasting.

Example 19

AMPPD+Enhancing Reagent

Referring to the method of Example 1, a chemiluminescent composition was formulated with ultra-pure water as follows:

| | |
|---|---|
| 2-amino-2-methyl-1-propanol | 200 mM |
| AMPPD | 0.5 mM |
| $MgCl_2$ | 5 mM |
| hexadecyl dimethyl benzyl ammonium chloride | 5 g/L |
| Fluorescein Sodium | 5 mg/L |
| Proclin 300 | 0.5 g/L |
| pH was adjusted with HCl | to 9.5 |

Figure 2:
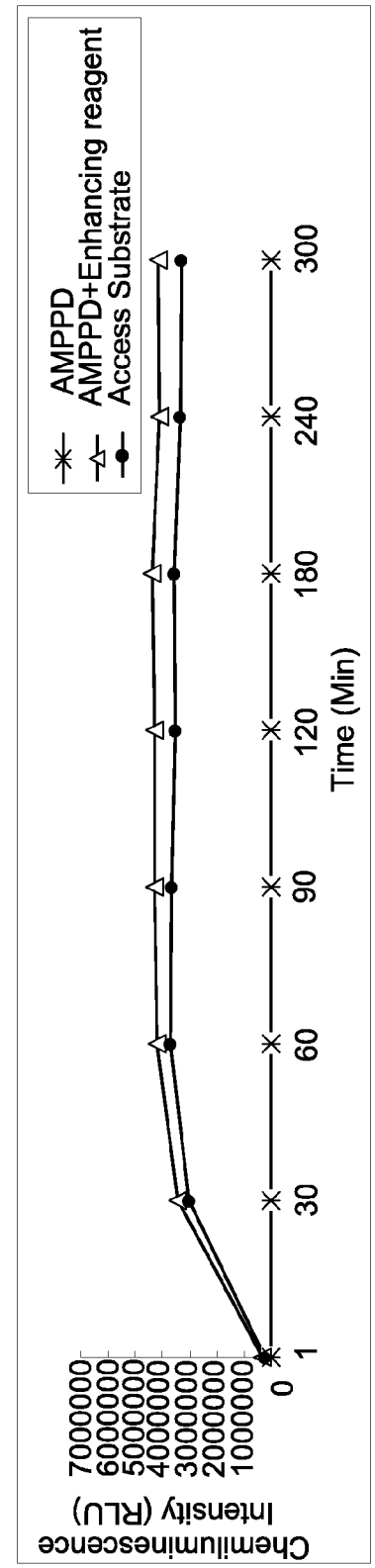
FIG. 2 is a comparison of luminescence signals of luminescent compositions with or without the enhancing reagent in Example 19, with a commercial luminescent composition control, wherein the X-axis is time and the Y-axis is luminescence intensity.

100 µl of the chemiluminescent composition was added to 20 µl of a 1 ng/mL solution of alkaline phosphatase. Chemiluminescence intensity was measured by a chemiluminescence analyzer. A commercial chemiluminescent composition, Access Substrate (Beckman), was also measured as a control for comparison. The results are shown in FIG. 2, which demonstrates that the enhancing reagent of the present disclosure enhances the luminescence signal of AMPPD, and that the performance of the chemiluminescent composition is similar to that of Access Substrate (Beckman).

Example 20

CSPD+Enhancing Reagent

Referring to the method of Example 1, a chemiluminescent composition was prepared with ultra-pure water as follows:

| | |
|---|---|
| 2-amino-2-methyl-1-propanol | 200 mM |
| CSPD | 0.25 mM |
| $MgCl_2$ | 5 mM |
| hexadecyl dimethyl benzyl ammonium chloride | 5 g/L |
| Fluorescein Sodium | 5 mg/L |
| Proclin 300 | 0.5 g/L |
| pH was adjusted with HCl | to 9.5 |

Figure 3:
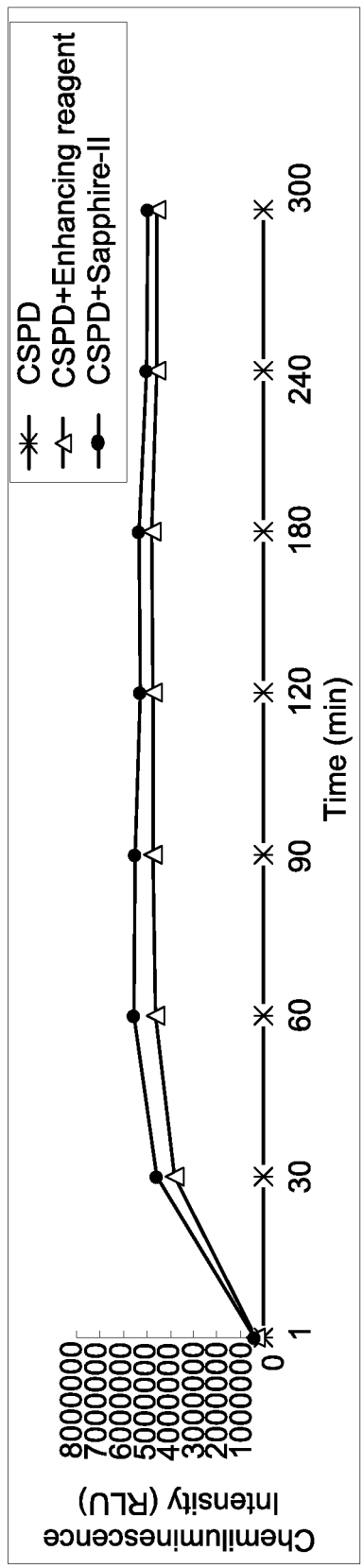
FIG. 3 is a comparison of luminescence signals of luminescent compositions with or without the enhancing reagent in Example 20, with a commercial luminescent composition control, wherein the X-axis is time and the Y-axis is luminescence intensity.

100 µl of the chemiluminescent composition was added to 20 µl of a 1 ng/mL solution of alkaline phosphatase. Chemiluminescence intensity was measured by a chemiluminescence analyzer. A commercial chemiluminescent composition, CSPD & Sapphire-II (Tropix), was also measured as a control for comparison. The results are shown in FIG. 3, which demonstrates that the enhancing reagent of the present disclosure enhances the luminescence signal of CSPD, and that the performance of the chemiluminescent composition is similar to that of CSPD & Sapphire-II (Tropix).

Example 21

CDP-Star+Enhancing Reagent

Referring to the method of Example 1, a chemiluminescent composition was prepared with ultra-pure water as, follows:

| | |
|---|---|
| 2-amino-2-methyl-1-propanol | 200 mM |
| CDP-Star | 0.25 mM |
| MgCl₂ | 5 mM |
| hexadecyl dimethyl benzyl ammonium chloride | 5 g/L |
| Fluorescein Sodium | 5 mg/L |
| Proclin 300 | 0.5 g/L |
| pH was adjusted with HCl | to 9.5 |

Figure 4:
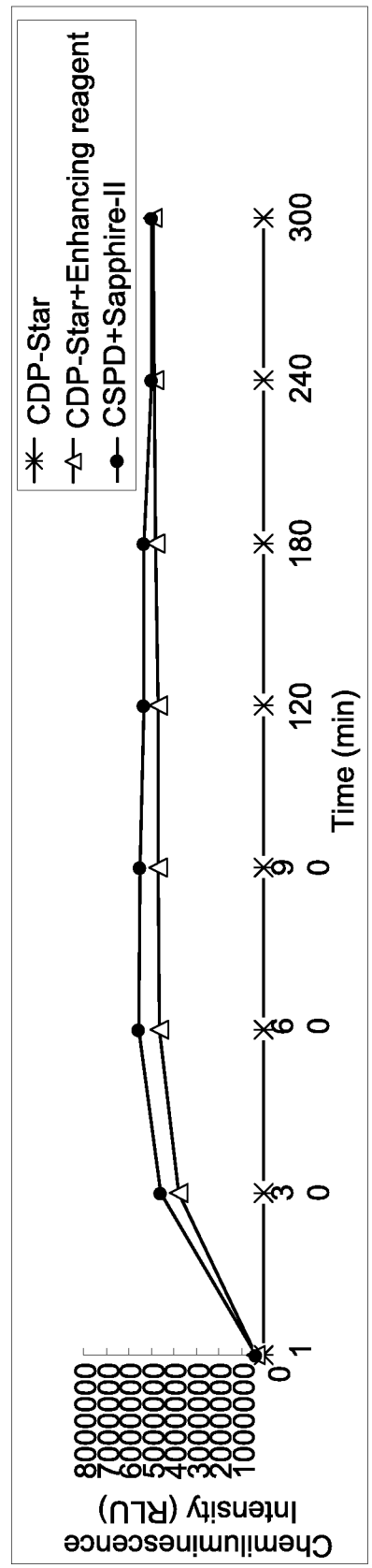
FIG. 4 is a comparison of luminescence signals of luminescent compositions with or without the enhancing reagent in Example 21, with a commercial luminescent composition control, wherein the X-axis is time and the Y-axis is luminescence intensity.

100 μl of the chemiluminescent composition was added to 20 μl of a 1 ng/mL solution of alkaline phosphatase. Chemiluminescence intensity was measured by a chemiluminescence analyzer. A commercial chemiluminescent composition, CSPD & Sapphire-II (Tropix), was also measured as a control for comparison. The results are shown in FIG. 4, which demonstrates that the enhancing reagent of the present disclosure enhances the luminescence signal of CDP-Star, and that the performance of the chemiluminescent composition is similar to that of CSPD & Sapphire-II (Tropix).

It can be seen from the examples above that alkyl dimethyl benzyl quaternary ammonium salts demonstrate good chemiluminescent enhancing effects for 1,2-dioxetane compounds, as well as unexpected synergistic enhancing effects in combination with fluorescent agents. Chemiluminescent compositions containing alkyl dimethyl benzyl quaternary ammonium salts can generate a strong luminescence signals, thereby improving the detection sensitivity of a diagnosis kit.

The data, figures, instruments, reagents and steps herein should be understood to be illustrative, but not restrictive. Although the present disclosure was described with references to the above concrete embodiments, many modifications and variances will be apparent to skilled persons in the art. All the modifications and variances also fall within the spirit and scope of the disclosure.

What is claimed is:

1. A chemiluminescent composition, comprising a 1,2-dioxetane compound having the structure:

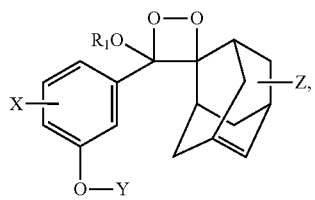

wherein $R_1$ is selected from alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, or halogenated alkyl acid; X is hydrogen or a substituent on phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on adamantane ring;

at least one alkyl dimethyl benzyl quaternary ammonium salt having the structure of General Formula I:

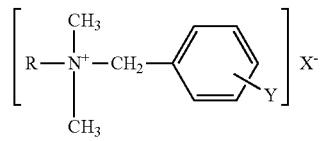

wherein:
R is selected from $C_{8-20}$ alkyl or $C_{8-20}$ alkenyl;
$X^-$ is a negative ion;
Y is a benzene ring substituent, each of which is independently selected from: hydrogen, halogen, hydroxyl, sulfhydryl, cyano, nitro, alkyl, alkoxy, haloalkyl, amino, alkylamino, and amido;
wherein the concentration of the alkyl dimethyl benzyl quaternary ammonium salt is in a range of between about 1 g/L to about 10 g/L; and
a fluorescent agent;
wherein the relative concentration of the alkyl dimethyl benzyl quaternary ammonium salt to the concentration of the fluorescent agent in the chemiluminescent composition is between about 1 g/L to about 2 g/L of alkyl dimethyl benzyl quaternary ammonium salt to about 1 mg/L of fluorescent agent.

2. The chemiluminescent composition of claim 1, wherein R is $C_{12-18}$ alkyl.

3. The chemiluminescent composition of claim 1, wherein $X^-$ is at least one of the following: a halide ion, $ClO_4^-$, $PF_6^-$, $CF_3SO_3^-$, $BF_4^-$, acetate, and p-toluene sulfonate.

4. The chemiluminescent composition of claim 1, wherein the alkyl dimethyl benzyl quaternary ammonium salt is selected from at least one of the following: a hexadecyl dimethyl benzyl ammonium salt, an octadecyl dimethyl benzyl ammonium salt, a dodecyl dimethyl benzyl ammonium salt, a myristyl dimethyl benzyl ammonium salt and combinations thereof.

5. The chemiluminescent composition of claim 1, wherein the alkyl dimethyl benzyl quaternary ammonium salt is selected from at least one of the following: hexadecyl dimethyl benzyl ammonium chloride, octadecyl dimethyl benzyl ammonium chloride, dodecyl dimethyl benzyl ammonium chloride, myristyl dimethyl benzyl ammonium chloride, dodecyl dimethyl benzyl ammonium bromide, myristyl dimethyl benzyl ammonium bromide, hexadecyl dimethyl benzyl ammonium bromide, octadecyl dimethyl benzyl ammonium bromide and combinations thereof.

6. The chemiluminescent composition of claim 1, wherein the chemiluminescent composition further comprises at least one of: 2-amino-2-methyl-1-propanol or a magnesium ion or both.

7. A chemiluminescent enhancing reagent configured to enhance the chemiluminescence of a 1,2-dioxetane compound having the structure:

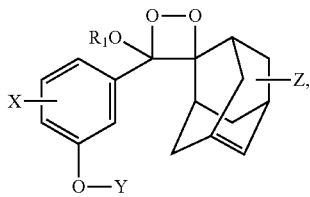

wherein R₁ is selected from alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, or halogenated alkyl acid; X is hydrogen or a substituent on phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on adamantane ring, wherein the chemiluminescent enhancing reagent comprises:

at least one alkyl dimethyl benzyl quaternary ammonium salt having the structure of general formula I:

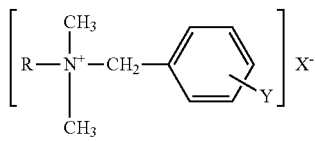

wherein:
R is selected from $C_{8-20}$ alkyl or $C_{8-20}$ alkenyl;
X⁻ is a negative ion;
Y is a benzene ring substituent, each of which is independently selected from hydrogen, halogen, hydroxyl, sulfhydryl, cyano, nitro, alkyl, alkoxy, haloalkyl, amino, alkylamino, and amido;
a fluorescent agent; and
a solvent configured to dissolve the at least one alkyl dimethyl benzyl quaternary ammonium salt, the fluorescent agent, and the 1,2-dioxetane compound;
wherein the final concentration of the alkyl dimethyl benzyl quaternary ammonium salt is in a range of between about 1 g/L to about 10 g/L; and
wherein the relative final concentration of the alkyl dimethyl benzyl quaternary ammonium salt to the final concentration of the fluorescent agent is between about 1 g/L to about 2 g/L of alkyl dimethyl benzyl quaternary ammonium salt to about 1 mg/L of fluorescent agent.

8. The enhancing reagent of claim 7, wherein R is $C_{12-18}$ alkyl.

9. The enhancing reagent of claim 7, wherein the alkyl dimethyl benzyl quaternary ammonium salt is selected from at least one of the following: a hexadecyl dimethyl benzyl ammonium salt, an octadecyl dimethyl benzyl ammonium salt, a dodecyl dimethyl benzyl ammonium salt, a myristyl dimethyl benzyl ammonium salt and combinations thereof.

10. The enhancing reagent of claim 7, wherein the alkyl dimethyl benzyl quaternary ammonium salt is selected from at least one of the following: hexadecyl dimethyl benzyl ammonium chloride, octadecyl dimethyl benzyl ammonium chloride, dodecyl dimethyl benzyl ammonium chloride, myristyl dimethyl benzyl ammonium chloride, dodecyl dimethyl benzyl ammonium bromide, myristyl dimethyl benzyl ammonium bromide, hexadecyl dimethyl benzyl ammonium bromide, octadecyl dimethyl benzyl ammonium bromide and combinations thereof.

11. The enhancing reagent of claim 7, wherein the enhancing reagent further comprises at least one of: 2-amino-2-methyl-1-propanol or a magnesium ion or both.

12. A kit for enhancing the chemiluminescence of 1,2-dioxetane compounds having the structure:

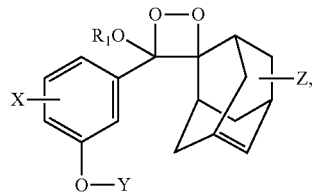

wherein R₁ is selected from alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, or halogenated alkyl acid; X is hydrogen or a substituent on phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on adamantane ring;

wherein the kit comprises:
at least one alkyl dimethyl benzyl quaternary ammonium salt having the structure of General Formula I:

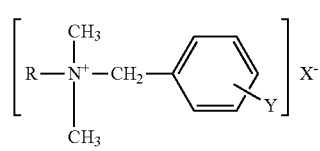

wherein:
R is selected from $C_{8-20}$ alkyl or $C_{8-20}$ alkenyl;
X⁻ is a negative ion;
Y is a benzene ring substituent, each of which is independently selected from: hydrogen, halogen, hydroxyl, sulfhydryl, cyano, nitro, alkyl, alkoxy, haloalkyl, amino, alkylamino, and amido;
a fluorescent agent; and
a manual instructing a user to mix the alkyl dimethyl benzyl quaternary ammonium salt with, the fluorescent agent and a 1,2-dioxetane compound, wherein the final concentration of the alkyl dimethyl benzyl quaternary ammonium salt is in a range of between about 1 g/L to about 10 g/L, and wherein the relative final concentration of the alkyl dimethyl benzyl quaternary ammonium salt to the final concentration of the fluorescent agent is between about 1 g/L to about 2 g/L of alkyl dimethyl benzyl quaternary ammonium salt to about 1 mg/L of fluorescent agent.

13. The kit of claim 12, wherein the components of the kit are stored individually or in the form of one or more mixtures.

14. A method for enhancing the chemiluminescence of 1,2-dioxetane compounds having the structure:

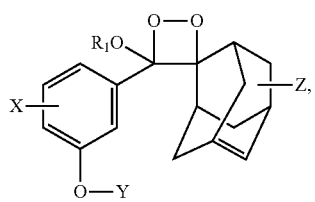

wherein $R_1$ is selected from alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, or halogenated alkyl acid; X is hydrogen or a substituent on phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on adamantane ring, wherein the method comprises:
providing at least one alkyl dimethyl benzyl quaternary ammonium salt having the structure of General Formula I:

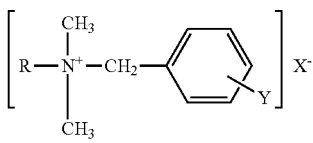

wherein:
R is selected from $C_{8-20}$ alkyl or $C_{8-20}$ alkenyl;
$X^-$ is a negative ion;

Y is a benzene ring substituent, each of which is independently selected from: hydrogen, halogen, hydroxyl, sulfhydryl, cyano, nitro, alkyl, alkoxy, haloalkyl, amino, alkylamino, and amido;

mixing the alkyl dimethyl benzyl quaternary ammonium salt with the 1,2-dioxetane compound;

mixing the alkyl dimethyl benzyl quaternary ammonium salt and the 1,2-dioxetane compound with a fluorescent agent; and dissolving the alkyl dimethyl benzyl quaternary ammonium salt, the fluorescent agent, and the 1,2-dioxetane compound in water, wherein the final concentration of the alkyl dimethyl benzyl quaternary ammonium salt is in a range of between about 1 g/L to about 10 g/L, and wherein the relative final concentration of the alkyl dimethyl benzyl quaternary ammonium salt to the final concentration of the fluorescent agent is between about 1 g/L to about 2 g/L of alkyl dimethyl benzyl quaternary ammonium salt to about 1 mg/L of fluorescent agent.

15. The method of claim 14, wherein R is $C_{12-18}$ alkyl.

16. The method of claim 14, wherein the alkyl dimethyl benzyl quaternary ammonium salt is selected from at least one of the following: hexadecyl dimethyl benzyl ammonium chloride, octadecyl dimethyl benzyl ammonium chloride, dodecyl dimethyl benzyl ammonium chloride, myristyl dimethyl benzyl ammonium chloride, dodecyl dimethyl benzyl ammonium bromide, myristyl dimethyl benzyl ammonium bromide, hexadecyl dimethyl benzyl ammonium bromide, octadecyl dimethyl benzyl ammonium bromide and combinations thereof.

17. The method of claim 14, further comprising mixing the alkyl dimethyl benzyl quaternary ammonium salt and the 1,2-dioxetane compound with at least one of: 2-amino-2-methyl-1-propanol or a magnesium ion or both.

* * * * *